United States Patent [19]

Romano

[11] Patent Number: 4,941,466
[45] Date of Patent: Jul. 17, 1990

[54] CURVED BORE DRILLING METHOD AND APPARATUS

[76] Inventor: Jack W. Romano, 412 NE. 165th, Apt. #13, Seattle, Wash. 98155

[21] Appl. No.: 196,319

[22] Filed: May 20, 1988

Related U.S. Application Data

[63] Continuation-in-part of Ser. No. 37,697, Apr. 13, 1987, abandoned.

[51] Int. Cl.$^5$ .............................................. A61B 17/16
[52] U.S. Cl. ..................................... 606/80; 408/127; 408/146; 408/187; 606/96; 606/180
[58] Field of Search ............. 128/92 V, 92 VD, 92 R, 128/92 YD, 92 VK, 92 VJ, 303 R, 305; 175/61.75, 73, 74, 75; 408/1 R, 127, 136, 146, 147, 187, 188; 81/177.6

[56] References Cited

U.S. PATENT DOCUMENTS

| | | | |
|---|---|---|---|
| 1,223,938 | 4/1917 | Close | 82/1.5 |
| 1,698,952 | 1/1929 | Hoover | 173/50 |
| 1,822,330 | 9/1931 | Ainsle | 128/334 R |
| 2,291,413 | 4/1942 | Siebrandt | 128/83 |
| 2,666,430 | 1/1954 | Gispert | 128/83 |
| 2,747,384 | 5/1956 | Beam | 464/52 |
| 2,905,178 | 9/1959 | Hilzinger | 128/303 R |
| 3,554,192 | 1/1971 | Isberner | 128/83 |
| 3,628,522 | 12/1971 | Kate | 128/751 |
| 3,697,188 | 10/1972 | Pope | 408/230 |
| 3,815,605 | 6/1974 | Schmidt et al. | 128/305 |
| 4,257,411 | 3/1981 | Cho | 128/92 VD |
| 4,265,231 | 5/1981 | Scheller, Jr. et al. | 128/92 VD |
| 4,312,337 | 1/1982 | Donohue | 128/92 VD |
| 4,345,601 | 9/1982 | Fukuda | 128/339 |
| 4,421,112 | 12/1983 | Mains et al. | 128/92 VY |
| 4,541,423 | 9/1985 | Barber | 128/92 VD |
| 4,590,929 | 5/1986 | Klein | 128/92 R |
| 4,622,960 | 11/1986 | Tam | 128/92 VK |

FOREIGN PATENT DOCUMENTS

1168222 3/1983 U.S.S.R. .

Primary Examiner—Robert A. Hafer
Assistant Examiner—Kevin G. Rooney
Attorney, Agent, or Firm—James R. Vance

[57] ABSTRACT

A curved bore hole drilling apparatus and method utilizing two power driven drill shafts equipped with flexible shaft sections on the distal ends thereof with each flexible shaft section having a cutting tip. A semicircular channel shaped drill guide loosely engages each flexible shaft end section and is caused to rotate through an approximate 90° angle as the cutting tips are advanced. The drill guides are pivotally mounted for rotation in substantially the same plane end, when rotated through an approximate 90° angle so as to meet, the cutting tips of the associated rotating flexible drill bits form a curved semicircular bore hole which may extend through 180°. The flexible shaft sections and guides are then backed out of the bore and the bore may be used for attachment of a tie such as a wire or a suture which is passed through the bore. The drilling shafts and flexible shaft sections are mounted in parallel relation within a housing and are advanced toward the surface to be bored in a rectilinear direction normal to the surface to be bored. In a second embodiment the parallel flexible shaft sections are pulled through their arcuate paths by means of the channel shaped drill guides which are rotated by means of worm and pinion drives under control of the operator. Each flexible shaft section has a slotted connection with its associated power driven shaft and is advance by the drill guides against spring pressure. As the drill guides are backed out of the bore the flexible shaft sections are returned under spring pressure. Still another embodiment utilizes a channel shaped drill guide of approximately 180° circumference which is caused to rotate through 180° to form the bore hole into and out of the bone surface. In this embodiment, the drill and guide housing is located within an anchoring sleeve which resists the unbalanced drilling forces tending to laterally shift the drill shaft housing. The use of 180° arcuate drill guide and the anchoring sleeve enable the bore hole to be formed in a joint cavity using arthroscopic surgical techniques.

36 Claims, 5 Drawing Sheets

CURVED BORE DRILLING METHOD AND APPARATUS

BACKGROUND OF THE INVENTION

1. Field of the Invention:

This application is a continuation-in-part of U.S. Patent Application Ser. No. 037,697 filed Apr. 13, 1987 for Curved Bore Drilling Method and Apparatus, now abandoned.

This invention relates to an apparatus and method for drilling a curved bore hole into the surface of a hard material such as bone or other solid material. The invention is more particularly directed to a drilling apparatus which guides a normally straight flexible drill shaft from a rectilinear approach path through a predetermined curved path as it is advanced into the material. This method and apparatus is of special utility in situations of severe space limitations since the drill shaft or shafts may be advanced through a first approach path which may be at right angles to the surface being bored and then through its curvilinear path, without movement or angular displacement of the drilling apparatus. One or more flexible drill shaft sections may be guided through curvilinear paths so as to form a semicircular hole into-and-out-of the surface to permit the attachment of a tying device or the like to the surface. Although the invention has a wide range of applications, it has special application in surgical procedures where a ligament or other tissue must to be secured to a bone surface for knitting. The present device permits such procedures to be accomplished in areas of limited access with minimum damage to bone and surrounding tissue. With the bore hole formed by the present invention, a suture or other attaching filament may be easily passed through the curved bore to anchor the tissue or ligament.

2. Description of the Prior Art:

In the field of orthopedic surgery it is often desirable to either secure tissue such as ligament to a bone surface, to immobilize adjacent bone structures or to reduce a fracture by passing a filament such as a suture or a wire through drilled holes in the bone surface. The Scheller, Jr, et al U.S. Pat. No. 4,265,231, issued May 5, 1981 lists a number of specific examples of such operations wherein a curved bore is advantageous and describes one known method and apparatus for forming curved bore holes. The Scheller device is an example of the use of a flexible drill-containing cannula of a predetermined curvature which may be hand manipulated through its curved path through the bone surface. As may be appreciated, the manipulation of such a cannula requires a considerable amount of space and it is thus of limited utility where access is limited. The space requirement for operation of the instrument also necessitates a considerabley larger skin incision. Not only does the manipulation of the hand held cannula and drive motor require additional space but the cumbersome size and shape of the cannula itself limit its utility. Other examples of the use of a rigid curved cannula are illustrated in the Barber U.S. Pat. No. 2,541,423, issued Sept. 17, 1985 and the Donohue U.S. Pat. No. 4,312,337, issued Jan. 26, 1982. These devices suffer from the same limitations discussed relative to the Scheller method and apparatus. In all of these methods and apparatus, the cannula is used to pull or advance the drill shaft through a curved path determined by the operator's manipulation of the entire instrument considering the shape of the preformed cannula. In spite of the various prior art devices discussed, the commonly used method of securing a suture or a wire to a bone surface is that of independently drilling two straight intersecting holes disposed at some angle less than 180°. A curved needle is then gradually forced through from one bore hole to the other. The problem with this type of approach is that it is often a hit or miss proposition and it is time consuming if the bore holes do not intersect or if the permitted working area is restricted. In some instances severe damage can also be done to the bone and/or the surrounding soft tissue. It is also possible to break a needle by using too much force, necessitating the retrieval of needle fragments.

The primary problems with prior art methods and apparatus are therefore the time consuming nature of the procedures, the inability to operate in a restricted area, and the possibility of severe damage to bone and/or surrounding tissue. The results of these drawbacks may have far reaching effects in terms of the cost of the surgery, the degree of scarring and the recovery and rehabilitation time required as well as anesthesia risks. Furthermore, modern day trends of reduction of incision size and decrease in tissue violation do not lend themselves to the sometimes crude and inexact methods in practice or any of the prior art described. In the practice of arthroscopic surgery for instance, an instrument is inserted into a joint cavity through an extrememly small incision, large enough only for the instrument. The cavity and manipulaton of the instrument is observed by means of a scope device inserted through a second near puncture size incision. Bone drilling under these conditions is presently difficult if not impossible with known bone drilling devices.

SUMMARY OF THE INVENTION

The present invention provides method and apparatus whereby a flexible drill shaft may be caused to enter the surface of a bone or other hard material in a first approach direction normal or at a given angle to the surface of the material and to then be guided through a second curvilinear path having a predetermined degree of curvature. With this method it is unnecessary to alter the angle of approach of the drill shaft during the procedure making it possible to drill a bone surface for instance through a very small and deep incision. The method further contemplates bore drilling in connection with arthroscopic surgery. Thus, in one form of the apparatus, a single arcuate drill guide of approximately 180° circumference is first set in position so as to be insertable through an anchoring sleeve located in an extremely small incision giving access to a joint cavity. Once located within the cavity, the 180° arcuate guide is returned to a start position and the flexible drill shaft is guided through an approximate 180° curvature bore hole, into-and-out-of the bone surface. The drill and guide are then backed out of the hole, and the drill guide member is returned to the initial approach position and drawn back through the anchoring sleeve or withdrawn with the sleeve from the joint cavity.

The flexible drill shaft section is connected to an elongated rigid shank or shaft section which in turn is driven by a conventional drive motor assembly. The drive motor assembly may be any one of many hand held drive motor units commonly utilized in surgical or dental drilling procedures. In one embodiment, the device provides for simultaneous advancement of the drill shaft and a curved channel shaped drill guide loosely coupled to the distal end of the flexible drill shaft section. In this manner, as the flexible drill shaft section advances, it is caused to follow the path of the preformed drill guide so as to form a curved bore without manipulation of the original angle of approach of the drill shaft. The drill shaft and guide member are then withdrawn after formation of the curved bore in the body of the material. In this particular embodiment of the invention, two such drill shaft and guide units are operated simultaneously with the curved drill guides being rotated in the same plane so as to cause the simultaneously formed curved bores to connect. A linkage is provided whereby the drill shaft or shafts and the drill guide or guides are advanced simultaneously with a single hand motion. This mechanism is housed in a housing unit the end or tip of which seats on the surface to be drilled. In a second embodiment of the invention, a spring biased slidable connection is provided in the drill shaft sections which permits the flexible shaft section to be pulled by means of the guide members through their arcuate paths to form the curved bores. The drill guide units are driven by means of worm and gear drives which may be connected to be operated by a trigger mechanism in a hand held device. Upon reverse direction operation of the guide units, the flexible drill shaft sections are allowed to be returned by their spring connecting means to withdraw the cutting means.

In a third embodiment of the invention, a single curved channel drill guide of approximately 180° in circumference is utilized. The drill guide in this embodiment operates to pull the flexible drill section and push the cutter means in the manner just described. The drill guide unit is driven by a single finger trigger-operated guide advancement means which powers the rotary drive means such as utilized in the previous embodiments. Since the drilling pressure reaction forces are unbalanced, the single guide unit may be operated within an anchoring sleeve which is anchored to the bone surface by known pinning methods. The advantage of the single guide member is that of the ability to insert the drilling apparatus through an incision which is approximately one half the length of that needed for the double drill guide unit embodiment. Utilizing the anchoring sleeve, this embodiment of the drilling apparatus may be inserted into extremely small size incisions in conjunction with arthroscopic surgery.

The procedure for curved bore hole drilling in both conventional and arthroscopic surgery is thus simplified and accomplished with extreme accuracy and minimum damage to bone and tissue. In modern day surgical procedures emphasis is being placed on efficiency and overall time saving due to pressure for medical cost reductions. Any reductions in time and increase in accuracy and efficiency is therefor of great significance. Further, the modern trend is toward procedures which reduce incision size and tissue violation. The latter trend is demanded not only for cost reduction and shortened recovery time but also reduction of scarring, rehabilitation and anesthesia risk have become major concerns. The present method and apparatus enables the attachment of filament to bone in an exact and efficient manner saving time and costs and permits such operation in very small and deep incisions, heretofore impossible with prior art devices.

DESCRIPTION OF THE PREFERRED EMBODIMENTS

Figure 1:
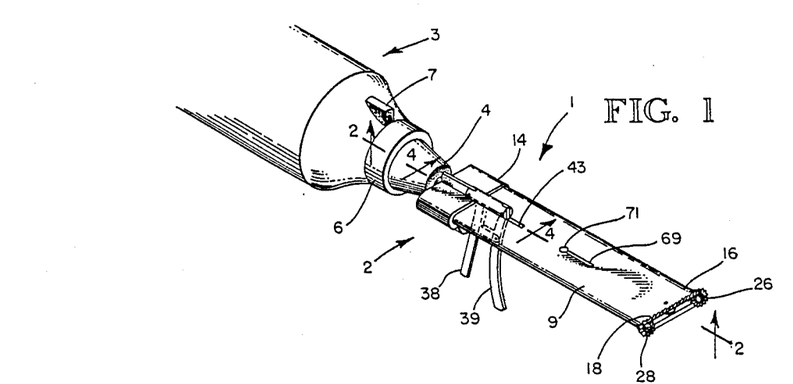
FIG. 1 is a perspective view of a first embodiment of the drilling apparatus and power drive unit.

Referring to the first embodiment shown in FIGS. 1-8, the apparatus as illustrated in FIG. 1, includes the drill shaft housing 1, the drill shaft and drill guide advancing mechanism 2 and the power drive unit such as an electric or pneumatic motor indicated generally at 3. The power drive unit 3 may be any one of many well-known electrical drive motors utilized in dental and surgical procedures which are of a size so as to be conveniently hand held. The power drive unit includes the jaws 4 which may comprise an adjustable grip such as a collet type collar operated by the adjustable ring 6 or a jacobs chuck in a conventional manner well understood to those versed in the art. The unit 3 will include an on/off switch 7 or variable speed trigger and the jaws 4 serve to connect the power drive to an input drive shaft 8 for the drilling apparatus presently to be described in detail.

Figure 2:
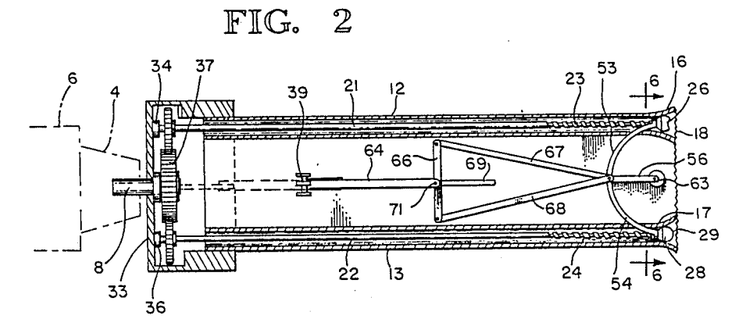
FIG. 2 is cross-sectional view taken along lines 2—2 of FIG. 1.
Figure 6:
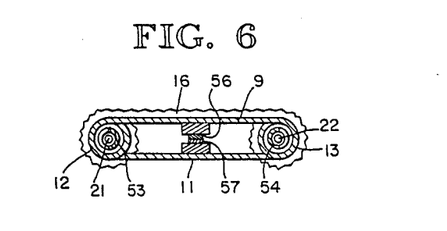
FIG. 6 is a cross-sectional view taken along lines 6—6 of FIG. 2.

The drill shaft housing 1 may be constructed of thin sheet metal and, as seen in FIGS. 1, 2 and 6 is elongated and generally flat in cross-section having the flat spaced sidewalls 9 and 11 either connected to or integral with the internal tubular sections 12 and 13 which form the rounded side edges of the hollow housing. The upper end of the housing 1 as seen in FIG. 2 is smooth or flat so as to telescopingly receive the gear housing portion 14 of the drill shaft and guide advancing mechanism 2 presently to be described. The gear housing 14 and the drill shaft housing 1 are in a slidable telescoping relationship. The lower or bottom end of the drill shaft housing 1 is flared around its outer periphery as indicated at 16 in FIGS. 2 and 3. Likewise the inner curved ends of the tubular sections 12 and 13 will also be flared as at 17. The bottom edge of the flared sections 16 and 17 are also provided with serrations or saw tooth formations 18 which permits the housing 1 to be seated firmly on the surface of a material such as bone material 19 which is to be drilled. Serrations 18 insure that a slight down pressure against the housing 1 will firmly engage the bottom end of the housing against the surface to prevent slippage.

Figure 3:
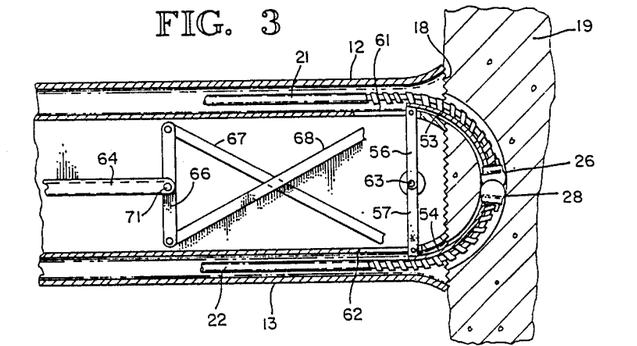
FIG. 3 is a cross-sectional view similar to FIG. 2 which illustrates the operation of the drill guide advancing mechanism.
Figure 7:
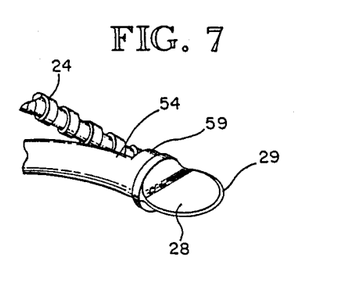
FIG. 7 is an isometric detail of the flexible drill shaft section having a convex cutting tip and its relationship to the associated drill guide.
Figure 8:
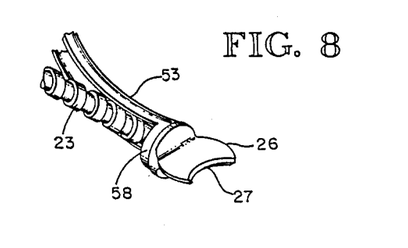
FIG. 8 is a detail perspective of the flexible drill shaft section having a concave cutting tip and its relationship with the associated drill guide.

In the FIG. 1-8 embodiment, each tubular housing 12 and 13 is equipped with an elongated drill shaft section 21 and 22 respectively which extends the full length of the housing. Each drill shaft 21 and 22 is provided with a flexible distal end portion 23 and 24 respectively which may be displaced in a curvilinear path for curved bore hole formation. The rigid drill shaft sections 21 and 22 may be formed of any suitable material such as stainless steel which is commonly used in orthopedic drilling procedures and may range in size from a diameter of 1/16 to ¼ inch for example depending upon the particular procedure or bore hole diameter requirement. The flexible shaft sections 23 and 24 may be welded or otherwise attached to the bottom ends of the rigid drill shaft sections and may be formed from helically grooved or slotted small diameter rods as illustrated in the present embodiment or, in some instances, may be formed from coil spring as is well known in the art of curved bore hole drilling. The distal end of each flexible section 23 and 24 is provided with a cutting tip or burr which does the actual cutting as it is advanced through the material. In the present embodiment, the cutting tip 26 is made from a flattened metallic material which has been suitably hardened for the cutting function. As shown in FIGS. 2, 3 and 8, the tip 26 has a concave cutting surface 27. The flexible end section 24 is provided with a flattened cutting tip 28 shown in detail in FIG. 7 which has a convex cutting surface 29 such that, when the cutting tips are brought into proximity, a bore hole is completed as shown in FIG. 3.

The upper ends of the drill shafts 21 and 22 are provided with gears 31 and 32 respectively and are journal mounted to the inside surface of the end plate 33 of the housing 14 so as to move with the housing 14 when the housing is telescoped relative to the housing 1. Journal blocks 34 and 36 may be provided for this purpose. The gears 31 and 32 are driven by a drive gear 37 mounted on the end of the input shaft 8 gripped by the jaws 4 of the electrical motor. The input shaft 8 may be suitably journaled in the end plate 33 as illustrated. With this arrangement, it will be noted, that the drill shafts 21 and 22 are rotated in the same direction during the drilling operation and may be advanced and retracted by producing relative movement between the housing 14 and the housing 1.

Figure 4:
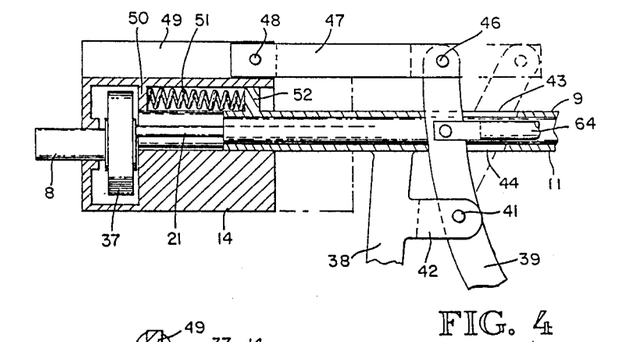
FIG. 4 is a cross-sectional view taken along lines 4—4 of FIG. 1.
Figure 5:
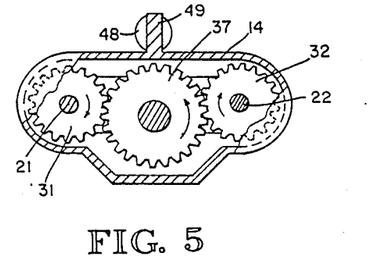
FIG. 5 is a partially sectioned end elevational view of the drill shaft drive gear arrangement.

As shown in FIGS. 1 and 4, the housing side wall 11 is provided with a fixed handle or grip 38 which may be welded or otherwise anchored to the housing wall. A second curved movable handle 39 is pivoted at 41 along its mid-section to an extension 42 of the handle 38 with its upper end extending through the slots 43 and 44 in the walls 9 and 11 respectively. The upper end of the handle or lever 39 is pivotally connected at 46 to a pull rod 47 which is in turn pivoted at 48 to an upstanding rib 49 affixed to the top wall of the housing 14. A compression spring 51 is seated against a housing shoulder 50 carried by the housing 14 and a dog 52 mounted on the top surface of the housing wall 9 as shown in FIG. 4. With this arrangement, the housing 14 and the housing 1 are biased apart by the spring 51 to the extent allowed by the movement of the lever 39 as shown in FIG. 4 and the two housings are telescoped together as illustrated by the dotted line portions in FIG. 4 by operation of the lever 39 when it is pivoted toward the fixed lever 38 by hand motion. This reciprocal movement of course advances the drill shafts.

Referring in particular to FIG. 2, the drill shaft guides comprise the arcuate channel shaped members 53 and 54 mounted on the radius arms 56 and 57 respectively. These arms are pivotally connected to the housing wall members 9 and 11 as illustrated in FIG. 6. Each drill guide 53 and 54 comprises a curved cross-section channel as illustrated more clearly in detail in FIGS. 7 and 8 and are provided with end collars or rings 58 and 59 respectively. The collars loosely engage the flexible drill sections 23 and 24 respectively as shown in FIGS. 7 and 8. The open side of the channels permits the drill guide member to intersect the path of the flexible drill sections and the loose rings or collars on the end of the channels retains the rotating flexible drill shaft sections within the guide channels as the guide channels are pivoted through their arcuate paths to form the curved bore holes. The arcuate drill guides 53 and 54 extend through suitable slots 61 and 62 in the lower ends of the tubular sections 12 and 13 respectively as shown most clearly in FIG. 3.

The linkage for simultaneously operating the arcuate drill guides with the forward movement of the drill shafts is illustrated in FIGS. 2 and 3. As previously described, the drill guides 53 and 54 are carried on radius arms 56 and 57 respectively. The radius arms are pivotally mounted at a common pivot point 63 near the bottom end of the drill shaft housing. As shown in FIG. 3, when the radius arms 56 and 57 are rotated from the vertical to the horizontal position, the channels 53 and 54 move with the advancing flexible drill shaft cutting tips to form a continuous bore through the surface and body of the material 19. It will be understood that, in the particular embodiment illustrated, the channel numbers 53 and 54 do not pull the flexible drill shaft sections through the curved path but, rather, are caused to move substantially simultaneously with the drill shafts as they are advanced by the drill guide advancing mechanism 2 previously described. The collars 58 and 59 on the ends of the channels 53 and 54 respectively guide the flexible drill shaft sections through their curved path while allowing the cutting tips 26 and 28 to rotate. As shown in FIG. 3, the width of the cutting tips are slightly larger than the diameter of the guide channels so as to provide adequate clearance for the channels as they are advanced through the bores formed by the cutting tips. The concave and convex forward cutting surfaces 27 and 29 respectively on the cutting tips enable the drill shafts to make a complete through bore upon being brought into close proximity.

In order to advance the drill guides simultaneously with the advancing of the drill shafts 21 and 22, the movable handle 39 is pivotally connected adjacent its upper end to push rod 64 to provide the downward motion for moving the drill guides. The push rod 64 is connected at its distal end to the drill guides by means of the crossarm 66 and pivoted drive links 67 and 68. The push rod 64 is guided in its rectilinear motion by means of the slot 69 in the housing wall 9. A pin member 71 extends through the push rod 64 and crossarm 66 and is in retained in the slot 71 as shown in FIG. 1. The crossarm 66 is held ridged or fixed to the rod 64 by means of the pin 71 or may be otherwise rigidly connected to the push rod. As viewed in FIGS. 2 and 3, the two pivoted links 67 and 68 have their upper ends pivotally connected to the crossarm 66 and their lower ends connected respectively to one of the drill guide arms at the junction of the associated guide arm and its radius arm. The link 67 is connected to the guide 54 and the link 68 is pivotally connected to the guide 53. As the push rod 64 is advanced simultaneously with the drill shafts, the links 67 and 68 serve to rotate the guide channels and radius arms in opposite directions about the pivot 63. Once the bore has been completed, the handles 38 and 39 may be released and the spring 51 will return the gear housing 14 which pivots the lever 39 counterclockwise as seen in FIG. 4 to simultaneously retract the push rod 64.

The overall operation of the FIG. 1-8 embodiment of the device is rapid and simple. In a typical surgical procedure the location for the bore hole is selected, the instrument is placed on the bone surface and held in place with one hand by grasping the drive unit 3. The serrated bottom edge 18 of the drill shaft housing prevents slippage of the instrument on the bone or other surface without the necessity of excess pressure. With the other hand, the operator simply grasps the handles 38 and 39 and, with the drive motor in operation, squeezes the handles together. The hand held drive unit is allowed to follow the advance of the drill shafts. The device is held in this position throughout the drilling operation and need not be further manipulated. This is of great importance in a restricted access situation such as in the case of the need for a deep incision to gain access to a bone surface. The drill shafts 21 and 22 will advance in unison and simultaneously the push rod 64 will operate to pivot the guide channels 53 and 54 through their arcuate paths until the cutting tips 26 and 28 have completed their course of travel and are in close proximity as shown in FIG. 3. Once the bore hole is completed, the handles 38 and 39 are released and the drill shafts retract by action of the spring 51. The device may then be lifted from the surface leaving the completed bore hole ready for a suture or other attachment means.

Figures 9, 10:
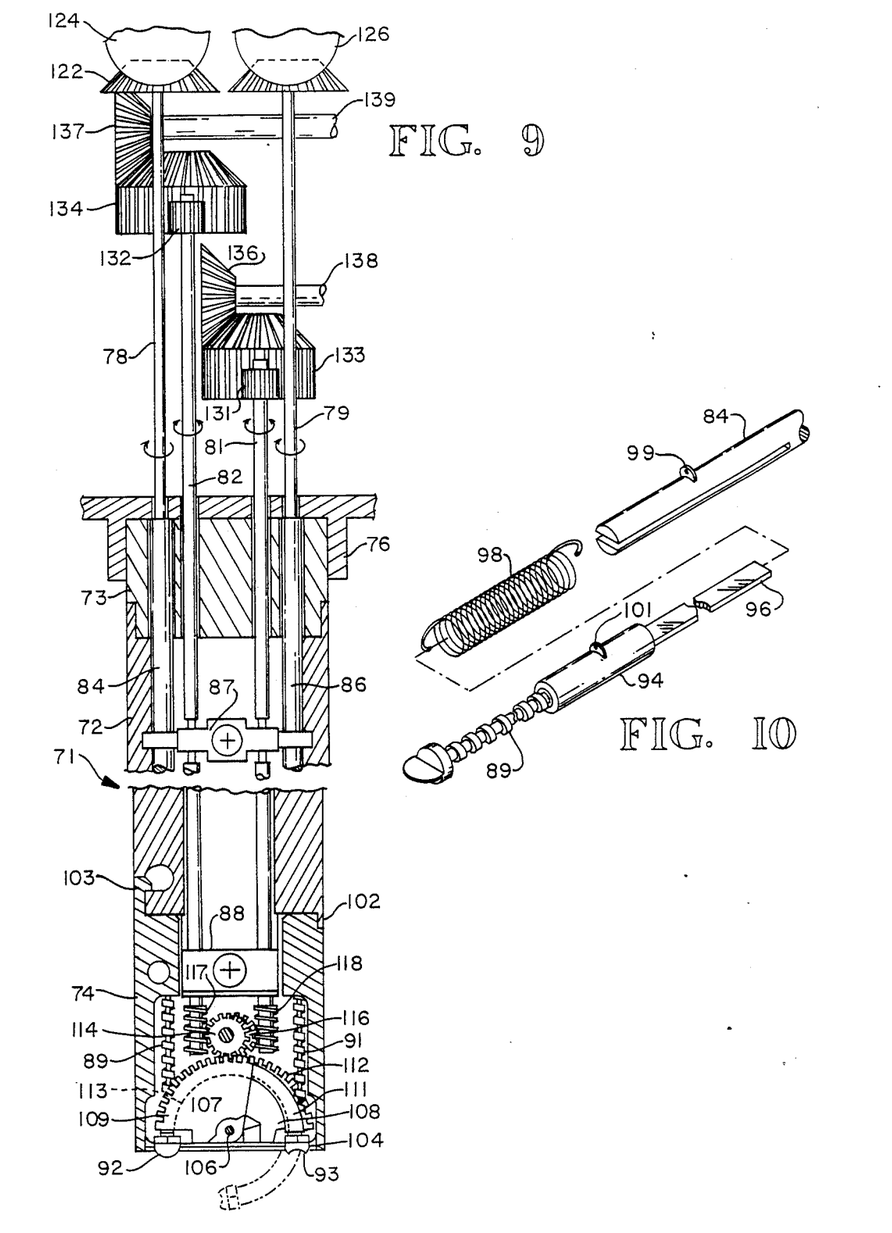
FIG. 9 is a partially sectioned side elevation of a second embodiment of the drilling apparatus according to the invention.
FIG. 10 is an exploded view of the slidable spring biased drill shaft connection.
Figure 11:
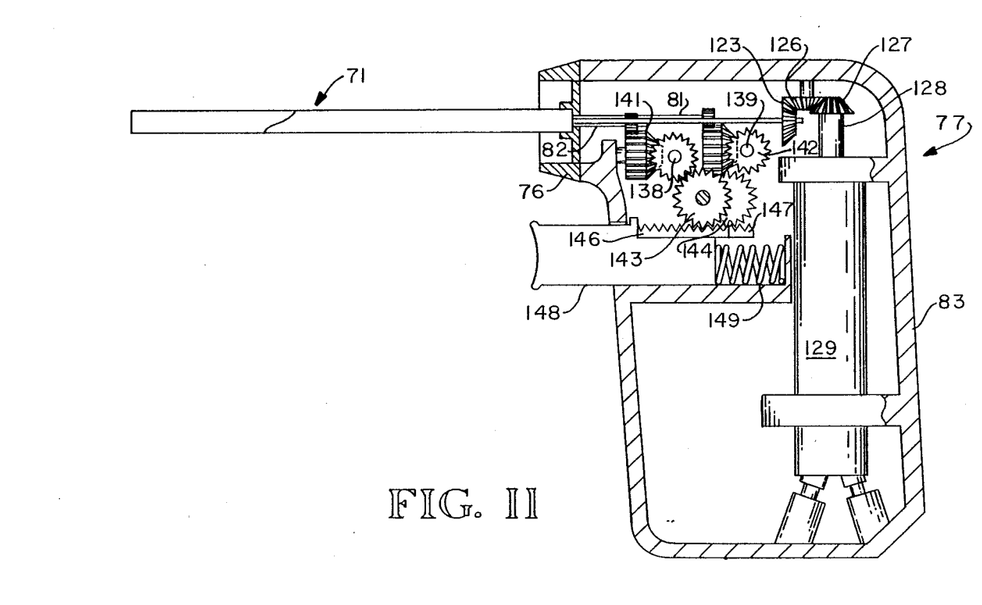
FIG. 11 is a partially sectioned side elevation showing the drive unit for the drilling apparatus of FIG. 9.

FIGS. 9-11 illustrate a second embodiment of the curved bore drilling apparatus wherein the flexile shaft sections and cutting tips are respectively pulled and pushed through their arcuate paths by the action of the shaft guide members. The flexible and rigid shaft sections have a spring biased sliding connection which allows the flexible sections to be pulled through their curved paths against spring pressure and to be returned by the same spring pressure upon return of the arcuate guide members. Referring first to FIG. 9, the embodiment includes a drill shaft housing unit shown generally at 71 which may be rectangular in cross-section similar to the housing 1 of the previous embodiment and includes a hollow central tubular section 72, an upper shaft support and bracing cap 73 and a bottom drill guide housing section 74. The drill shaft housing 71 is received in the outdrive fitting 76 of a hand-held drive unit indicated generally at 77 in FIG. 11. The cap 73 may be received in a suitable socket in the fitting 76 by means of a press fit or any other suitable retention means. As seen in FIG. 9, the outdrive fitting 76 provides support for the two rigid rotary drill shafts 78 and 79 as well as the drill guide rotary drive shafts 81 and 82 presently to be described in detail. These four shafts are provided with suitable mating supports not shown, within the housing body 83 of the unit 77 shown in FIG. 11. The drive shafts 78 and 79 include large diameter lower end portions 84 and 86 respectively which extend through the cap 73 and are mounted for rotation therein. Likewise, the drill guide drive shafts 81 and 82 pass through the cap 73 and into the lower tubular section 72 of the housing. It will also be understood that the shafts 81 and 82 are mounted for rotation within the cap 73. The four rotary shafts are supported along their length within the upper extent of the hollow tubular section 72 by means of the spanner bearing support and shaft brace 87 in a well known fashion and the lower ends of the drill guide drive shafts 81 and 82 are supported in a second spanner bearing support and shaft brace 88 in the drill guide housing 74. It will be understood that the spanner bearing support and shaft braces may be of any conventional design well known in the art and are designed to rotatably support the respective shafts within the housing. The lower ends of the drive shaft sections 84 and 86 pass through suitable bores or channels in the lower end of the housing section 72 and the drill guide housing section 74. These bores or channels will be of sufficient diameter to permit rotation of the drive shafts and reciprocation of the drill shafts during the drilling operation. FIG. 10 illustrates the details of the slidable coupling of the drill shafts and it will be understood that the same connection is utilized with respect to drill sections 91 and 86.

Referring to FIG. 10, the flexible drill shaft sections 89 and 91 may be formed from any well known materials such as described with respect to the FIGS. 1-8 embodiment and will include the cutting tips 92 and 93 which may also be identical to that described with respect to the previous embodiment. In order to provide for a sliding fit between the flexible section 89 and the rigid section 84, the flexible section 89 is connected to the rigid coupler portion 94 of the rigid shaft section 84. The coupler 94 includes a flat extension 96 which is telescopically received in an elongated slot 97 in the drive shaft section 84. In this manner, well known in the art, the drive shaft 84 transmits rotary motion to the flexible drill shaft portion and allows for a linear sliding movement of the coupler 94 and the flexible shaft. In order to bias the coupler 94 into engagement with the shaft section 84, the tension spring 98 surrounds the lower end of the shaft section 84 and the upper end of the coupler 94 and will be attached to the two members by means of the eyelets 99 and 101 formed in suitable brackets on the mating members. This relationship is shown by the exploded view of FIG. 10. It will also be understood that the bores or channels in the housing 72 and 74 are of sufficient diameter to permit rotation of the shafts with these protrusions. Although the slidable connection is shown and described as being between the coupler and rigid shaft sections, it will be obvious to those skilled in the art that such a connection may be provided at any point along the rigid or flexible shafts in order to allow the flexible shaft to be pulled through its arcuate path and returned.

The drill guide housing 74 as previously described includes the spanner bearing support and shaft bracing block 88 for receiving the drive shafts 81 and 82. The drill guide housing may be connected to the tubular section 72 in any suitable manner such as the circumferential flange 102 and the clip member 103 which is a well understood expedient in the art. The lower end of the housing 74 is open to permit operation of the flexible drill sections and drill guides as previously described relative to the FIGS. 1–8 embodiment. The bottom peripheral edge face 104 may also be knurled (not shown) or otherwise serrated or roughened in order to provide a gripping engagement on the surface of a bone or other material to which the drilling unit is applied. The bottom end of the housing 74 is provided with a cross shaft 106 for mounting the rotatoable drill guide members 107 and 108 on a common rotary axis. As viewed in FIG. 9, the drill guides may be identical and mirror images of each other so as to operate in opposite directions through an approximate 90° angle and in substantially the same vertical plane. To accomplish this, each drill guide includes a gear sector and an arcuate guide member laterally offset therefrom. Thus, the drill guide 107 has a gear sector 109 and a channel shaped arcuate guide 111 and the drill guide 108 has a reversely positioned gear sector 112. The arcuate channel guide 113 is located on the opposite side of the gear sector 109 as viewed in FIG. 9. With this arrangement, the drill guide 107 may be rotated approximately 90° in the clockwise direction and the drill guide 108 may be rotated approximately 90° in the counter clockwise direction as view in FIG. 9. The gear sectors 109 and 112 are provided with meshing pinions 114 and 116 respectively which are mounted on laterally offset stub shafts so as to be positioned in mesh with worm drives 117 and 118 respectively. In this respect, it will be noted as shown in FIG. 11 that the drive shafts 81 and 82 are laterally offset in opposite directions so as to place the worm drives in full mesh with the laterally offset pinions 114 and 116.

The completion of an approximately 180° curved bore into and out of a bone or other surface utilizing the embodiment of FIGS. 9–11 will be substantially the same as that described for the previous embodiment. One method of driving the rigid drill shafts 78 and 79 is illustrated in FIGS. 9 and 11 wherein the shafts 78 and 79 are provided with bevel gears 122 and 123 respectively which are in mesh with mating bevel gears 124 and 126. The bevel gears 124 and 126 are driven by a common bevel drive gear 127 on the drive shaft 128 of a rotary pneumatic motor 129. The motor 129 may be of any well known commercially available design. This drive arrangement will rotate the drive shaft 78 and 79 in the same direction to drive the flexible drill shafts and cutting tips as described relative to the previous embodiment.

A trigger type rack and pinion drive is provided for rotating the drill guide members through their arcuate paths. In order to drive the shafts 81 and 82 in the same rotary direction the drive trains are substantially identical. The shafts 81 and 82 have pinions 131 and 132 respectively in mesh with spur gears 133 and 134 respectively. As illustrated most clearly in FIG. 9, each spur gear 133–134 has a bevel gear portion in mesh with bevel gears 136 and 137 respectively fixed to shafts 138 and 139. The opposite ends of the drive shaft 138 and 139 are provided with spur gears 141 and 142 respectively as seen in FIG. 11. These spur gears mesh with rack driven spurs 143 and 144 respectively. The spur gear 143 is rotated by means of the rack 146 and the spur 144 is driven by the parallel adjacent rack 147. Cross shafts for mounting the various spur gears and bevel gears described will be suitably journaled within the housing 83 in any manner well known to the art. The racks 146 and 147 are fixedly mounted on a trigger bar 148 slidably received in the housing 83. As illustrated, the trigger bar 148 is biased in the outward direction by means of the compression spring 149.

In the position illustrated in FIG. 9, the drill guide units 107 and 108 are in their retracted positions. Upon depressing the trigger 148 against the pressure of the spring 149, the racks 146 and 147 activate the drive shafts 81 and 82 to rotate the guide members 107 and 108 through their arcuate paths by means of the worm drives 117 and 118. As the guide members 107 and 108 advance through their arcuate paths, the rotating flexible drill sections 89 and 91, by virtue of the sliding connection in the shaft sections, are caused to advance through arcuate paths against the tension of spring 98. When the trigger bar 148 is released, the spring 149 returns the trigger bar to its original position shown in FIG. 11 which reverses the direction of the worm drives and consequently retracts the guide members 107 and 108. As the guide members return to their positions shown in FIG. 9, the springs 98 cause the flexible drill sections to return to their original positions shown in FIG. 9. With this arrangement, the curved bore hole drilling is accomplished with one hand in a rapid and efficient manner utilizing the extremely small skin incision necessary to insert the drill shaft housing 71.

Figures 12, 14:
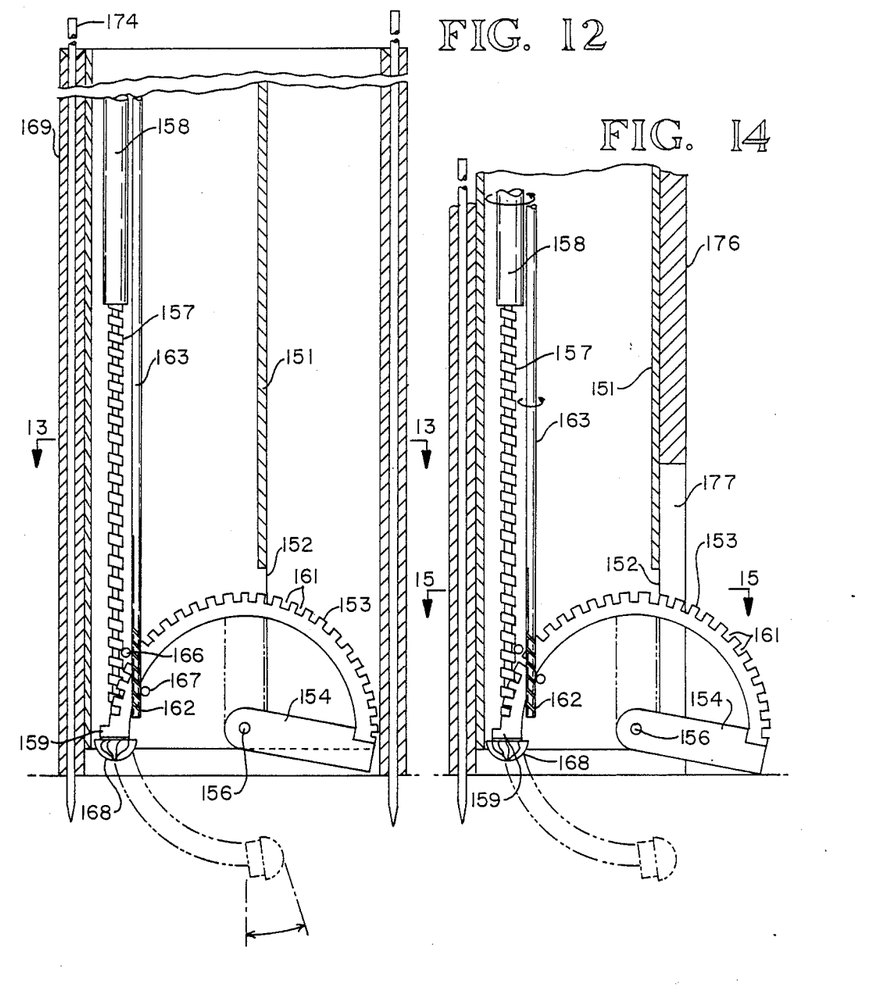
FIG. 12 is a partially sectioned elevational view of a third embodiment of the invention wherein a single arcuate drill guide is utilized.
FIG. 14 is a partially sectioned elevational view of the single drill guide of FIG. 12 with an anchoring sleeve arrangement for inserting the drill apparatus through a small incision.
Figures 13, 15:
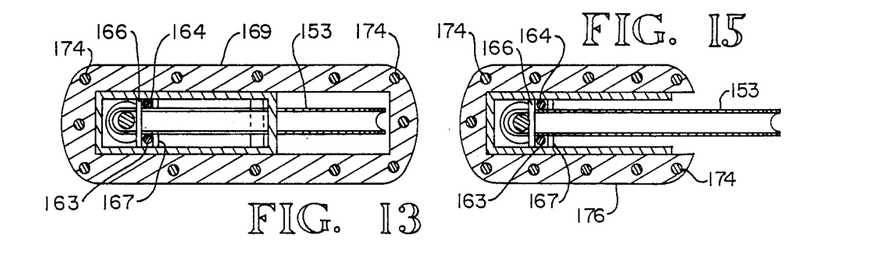
FIG. 13 is a cross-sectional view taken along lines 13—13 of FIG. 12.
FIG. 15 is a cross-sectional view taken along lines 15—15 of FIG. 14.

FIGS. 12 and 13 illustrate a third embodiment of the invention wherein an arcuate drill guide channel of approximately 180° may be utilized to form a curved bore into-and-out-of a bone surface. Another advantage of the single 180° drill guide is the ability to construct the drilling apparatus and housing so as to require only one-half the width of the double arcuate guide embodiments described. This ability for smaller space requirements enables the single 180° drill guide to be utilized effectively in arthroscopic surgery because of the extremely small puncture incision necessary.

The embodiment shown in FIGS. 12–15 are extremely simplified because of the elimination of one of the drill shafts and one of the drill guide members. The ability to advance a single flexible drill shaft through its curved path also reduces the number and complexity of the linkages involved. It will be understood that any drive means such as those shown and described in the previous two embodiments may be utilized, or adapted by one of ordinary skill in the art, to drive the single drill shaft and the double worm drive shafts to be described. The details of such drive mechanism are therefore omitted from the drawings for the sake of simplicity. Referring to FIG. 12, the drill shaft housing 151 may be a straight tubular section, rectangular in cross-section, and made from rigid material such as stainless steel. The tubular housing 151 will be understood to be connected to a hand held drive mechanism such as previously described. The bottom extent of one end wall of the tubular housing 151 is removed as at 152 to permit the approximate 180° rotation of the drill guide. The arcuate drill guide comprises a single channel shaped semi-circular member 153 having one end thereof welded or otherwise rigidly attached to the single radius arm 154. The arm 154 is pivotally attached at one end to the bottom end of the tubular housing 151 by means of the cross-shaft 156. A flexible drill shaft section 157 is located in the housing 151 and includes a coupler section 158. It will be understood that the coupler 158 is a part of the rigid drive shaft and that a tension spring biased slip connection is provided such as previously described relative to FIG. 10. The flexible drill shaft section 157 is thus spring biased upwardly as viewed in FIG. 12 and passes through the collar section 159 on the free end of the channel guide member 153. The flexible drill section 157 will be free to rotate within the collar 159 as the channel guide is caused to advance through its arcuate course.

As illustrated in FIG. 13, the channel member 153 is U-shaped in cross-section and each of the sidewalls of the U-section is provided with spaced radial slots 161 around substantially its entire periphery. These slots are designed to mesh with the helical threads 162 on the two helical drive shafts 163 and 164 which extend vertically in the housing 151 parallel with the flexible drill shaft 157. Any conventional means may be utilized to journal mount the drive shafts 163 and 164 and to provide a rotary drive therefore. In order to stabilize the bottom ends of the drive shafts 163 and 164 against reaction forces due to the advancement of the channel member 153, the cross pins 166 and 167 are provided and are vertically spaced, one above the channel member and one below. These cross pins 166 and 167 may be anchored in the sidewalls of the housing 151. With this arrangement, rotation of the helical drive shafts 163 and 164, both of which will be rotated in a direction to advance the channel member, will result in pulling the flexible drill shaft 163 through a curved path into the bone surface. The enlarged cutter tip 168 ensures that the drill shaft and the arcuate guide will be easily passed through the bore formed by the tip. The tip 168 extends beyond the 180° arc of the channel member 153 thus also ensuring that a complete rotation of the channel member through approximately 180° will form a through bore completely into-and-out-of the bone surface.

Since the drilling pressure is applied on only one side of the 180° guide channel, there is a tendency to produce lateral shifting of the drill housing 151 preventing maintenance of accurate location and stability throughout the drilling operation. For this reason, the housing 151 and the drill guide are inserted within a close fitting anchor sleeve 169. The anchor sleeve may be formed by any suitable construction such as that illustrated which provides vertical bores or passages for the insertion of anchoring pins. Such pins are known as Steinman pins and are commonly used to locate jigs or other appliances in preparation for bone drilling. A plurality of vertical passages provide for placement of a plurality of Steinman pins 174 placed at selected locations about the periphery of the anchoring sleeve as will be understood by those familiar with the art. Any suitable means may be utilized to provide for the placement of the pins and anchoring of the sleeve. In the embodiment of FIGS. 12 and 13, the sleeve 169 completely encloses the housing 151 and the arcuate guide 153 in its initial or starting position with the guide extending beyond the walls of the housing 151. In this mode of operation, the incision provided to gain access to the bone surface to be drilled must be only large enough to accommodate the shape of the guide channel and anchor sleeve as shown in FIG. 12.

FIG. 14 illustrates another embodiment wherein the anchoring sleeve 176 is wide enough to accommodate only the housing 151 and is provided with an opening 177 coextesive with the opening 152 of the housing 151. It will be understood that, except for location of the slot 152, the anchoring sleeve 176 is otherwise the same as anchoring sleeve 169 in cross-section to provide for insertion of Steinman pins. The embodiment of FIGS.. 14 and 15 has special utility in arthroscopic procedures wherein a scope is inserted through a puncture incision in a joint cavity and the anchor sleeve 176 is inserted through a separate puncture incision of a size to accommodate only the shape of the sleeve. The pin locating sleeve is initially inserted into the joint cavity and placed on the bone in the desired position. The Steinman pins are inserted through the sleeve by means of any conventional pin inserting apparatus. The drill guide 153 is then moved to the position where the radius arm 154 is substantially vertical as shown in the dotted line position in FIG. 14. This position allows the housing 151 to be inserted within the anchor sleeve 176. The housing is inserted through the sleeve until the drill guide is in a position to be rotated to the solid line position through the opening in the housing and the opening 177 in the sleeve as shown in FIG. 14, ready for drilling. The drill shaft housing is then seated on the surface of the bone to be drilled. The drilling operation may then be commenced. After the drill guide has been rotated through 180° and the curved bore hole formed, the guide is retracted to the full line position shown in FIG. 14 to remove the drill shaft and cutter means from the bore hole. The drill housing is then raised off the bone and the guide returned to the vertical dotted line position in order to permit removal of the housing from the anchor sleeve. The drill housing 151 is then withdrawn from the anchoring sleeve. The anchoring sleeve 176 may remain in the joint cavity for the purpose of admitting suture passing instruments or to relocate the sleeve to another desired location for further drilling operations.

Although the present invention has been described and illustrated with respect to specific embodiments thereof, it will be apparent to those skilled in the art that modifications may be made without departing from the spirit of the invention or from the scope of the appending claims.

What is claimed is:

1. An apparatus for drilling a curved bore within a material comprising:
   (a) rotary drive means;
   (b) drill shaft means having one end adapted for connection to said rotary drive means, said drill shaft means having a distal flexible end section;
   (c) cutting means secured to said flexible end section;
   (d) mounting means for directing said drill shaft means along a rectilinear path substantially normal to a surface of said material;
   (e) guide means carried by said mounting means to guide said flexible end section and said cutting means from said rectilinear path along a curved path to form said curved bore within said material, said rectilinear path having an angle of approach with respect to a surface of said material; and
   (f) means for pivotally moving said guide means along said curved path without requiring an alteration of said angle of approach.

2. An apparatus for drilling a curved bore within a material comprising:
   (a) housing means;
   (b) rotary drive means;
   (c) drill shaft means having one end adapted for connection to said rotary drive means, said drill shaft means having a distal flexible end section;

(d) cutting tip means secured to said flexible end section;

(e) means mounting said drill shaft means within said housing means for reciprocal movement therein;

(f) curved guide means located within said housing means adjacent to said flexible end section;

(g) means pivotally mounting said curved guide means within said housing for movement of said curved guide means along a curved path; and (h) means acting between said curved guide means and said flexible end section to guide said flexible end section and said cutting tip means along said curved path when said drill shaft means is reciprocated concurrently with pivoting said curved guide means.

3. The apparatus of claim 2, further comprising:
(a) first and second drill shaft means;
(b) first and second curved guide means, said first and said second curved guide means being generally arcuate;
(c) means pivotally mounting said first and said second curved guide means within said housing for pivotal movement of said first and said second curved guide means within a substantially common plane to enable corresponding flexible end sections and said cutting tip means to form said curved bore.

4. The apparatus of claim 2, wherein said curved guide means comprises:
(a) a curved channel member having one side open for reception of said flexible end section as said flexible end section advances, said curved channel member having a predetermined curvature of an intended curved bore; and
(b) radius arm means connected at one end thereof to said curved channel member and having another end thereof pivotally connected to said housing means;
(c) wherein another end of said curved channel member comprises engaging means to engage said flexible end section adjacent to said cutting tip means and to retain said cutting tip means therein.

5. The apparatus of claim 4, further comprising:
(a) first and second drill shaft means;
(b) first and second curved guide means, said first and said second curved guide means being generally arcuate;
(c) means pivotally mounting said first and said second curved guide means within said housing for pivotal movement of said first and said second curved guide means within a substantially common plane to enable corresponding flexible end sections and said cutting tip means to form said curved bore.

6. The apparatus of claim 4, wherein said cutting tip means in generally larger in diameter than said curved channel member,
said engaging means comprising a collar attached to an end of said curved channel member thereby securing said flexible end section to said curved channel member behind said cutting tip means,
whereby said curved bore formed by said cutting tip means is larger in diameter than said curved channel member to permit movement therethrough by said curved channel member as said cutting tip means advances, and said apparatus further comprising actuation means to advance said drill shaft means and to pivot said curved channel member simultaneously,
whereby said curved channel member guides said advancing flexible end section along said curved path.

7. The apparatus of claim 6, wherein said actuation means comprises:
(a) journal housing means for mounting driven ends of said drill shaft means, said journal housing means being mounted for reciprocal movement relative to said drill shaft means for advancing and retracting said drill shaft means;
(b) actuation lever means pivotally connected to said housing means and to said journal housing means for effecting said reciprocal movement;
(c) a push rod located within said housing means, said push rod being pivotally connected to said actuation lever means; and
(d) operating linkage means connecting said push rod to said curved guide means for rotating said curved guide means simultaneously with advancement of said drill shaft means.

8. The apparatus of claim 3, further comprising first and second cutting tip means mounted on said corresponding flexible end sections,
said first cutting tip means having a concave forward cutting surface, and
said first cutting tip means having a concave forward cutting surface, and
said second cutting tip means having a convex forward cutting surface,
whereby said curved bore is completed upon completion of travel of said cutting tip means.

9. An apparatus for drilling a curved bore within a material comprising:
(a) an elongated tubular drill shaft housing;
(b) drill shaft drive means;
(c) drill shaft means having a rigid shaft section adapted for connection to said drill shaft drive means at one end thereof and having a distal flexible end section connected to an opposite end thereof, said drill shaft means being contained within said drill shaft housing and guided for reciprocation along a rectilinear path therein;
(d) cutting tip means connected to a distal end of said flexible shaft section;
(e) a generally arcuate curved channel shaped guide member pivotally mounted within said housing adjacent to said cutting tip means for movement along a predetermined arcuate path which is generally tangential to said rectilinear path of said flexible end section, said guide member being in retaining engagement with said flexible end section behind said cutting tip means to guide said cutting tip means and said flexible end section through said arcuate path as said drill shaft means is advanced through said material; and
(f) actuation means carried by said drill shaft housing to simultaneously advance said drill shaft means and said guide member to form said curved bore, said cutting tip means being greater in diameter than said guide member to permit said guide member to move freely within said curved bore.

10. The apparatus of claim 9, wherein said actuation means comprises:
(a) journal housing means for mounting a driven end of said drill shaft means, said journal housing means being mounted on said drill shaft housing for relative reciprocal movement therewith for advancing and retracting said drill shaft means;
(b) actuation lever means pivotally connected to said drill shaft housing and to said journal housing means for effecting said reciprocal movement;
(c) a push rod in said drill shaft housing pivotally connected to said actuation lever means; and
(d) operating linkage means connecting said push rod to said guide member for pivoting said guide member simultaneously with advancement of said drill shaft means.

11. The apparatus of claim 10, further comprising:
(a) first and second drill shaft means;
(b) first and second curved guide members, said first and said second guide members being generally arcuate; and
(c) means pivotally mounting said first and said second guide members within said drill shaft housing for pivotal movement of said first and said second guide members within a substantially common plane to enable corresponding distal flexible end sections and said cutting tip means to form said curved bore.

12. The apparatus of claim 11, wherein said journal housing means comprises:
(a) gear means connected for simultaneously driving said first and said second drill shaft means; and (b) input drive shaft means adapted for connection to a power drive motor and to said gear means.

13. A method for forming a curved bore within a material, comprising the steps of:
(a) directing a drill shaft having a flexible distal end section with cutting means thereon as long a rectilinear approach path at a given angle of approach to a surface of said material;
(b) maintaining a portion of said drill shaft within said rectilinear approach path; and
(c) simultaneously guiding said flexible distal end section and said cutting means through a curved path, said cutting means forming a curved bore into said material, said drill shaft being capable of being advanced and retracted to form said curved bore without requiring an alteration of said angle of approach.

14. The method of claim 13, further comprising the steps of:
(a) simultaneously directing a second drill shaft having a flexible distal end section with cutting means thereon along a second rectilinear approach path which is generally parallel to said first rectilinear approach path; and
(b) guiding said the flexible distal end sections of said first and said second drill shafts within a common plane until said cutting means approach each other to form a curved bore.

15. An apparatus for drilling a curved bore within a material comprising:
(a) a rotary drive means;
(b) housing means;
(c) drill shaft means mounted for reciprocation along a rectilinear path within said housing means, said drill shaft means having one end adapted for connection to said rotary drive means, said drill shaft means having a distal flexible end section;
(d) cutting means secured to said flexible end section;
(e) a curved guide member pivotally mounted within said housing means adjacent said cutting means for movement in a predetermined curved path generally tangential to said rectilinear path of said flexible end sections, aid curved guide member being in retaining engagement with said flexible end section to guide said cutting means and said flexible end section away from said rectilinear path toward said predetermined curved path as said drill shaft means is advanced through said material.

16. An apparatus for forming a curved bore within a material comprising:
(a) cutting means;
(b) housing means;
(c) bore forming means mounted for reciprocation along a rectilinear path within said housing means, said bore forming means having a distal flexible end section with said cutting means associated therewith;
(d) a generally arcuate curved guide means pivotally mounted within said housing means adjacent to said flexible end section for movement along a predetermined arcuate path generally tangential to said rectilinear path of said bore forming means, said guide means being in retaining engagement with said flexible end section to guide said cutting means and said flexible end section along said predetermined arcuate path as said bore forming means is advanced through said material.

17. An apparatus for drilling a curved bore within a material comprising:
(a) housing means;
(b) cutting means;
(c) rotary drill shaft means mounted for reciprocation along a rectilinear path within said housing means, said rotary drill shaft means having a distal flexible end section whereupon said cutting means are attached;
(d) a curved guide means pivotally mounted within said housing means adjacent to said cutting means for movement along a predetermined curved path, said predetermined curved path being generally tangential to said rectilinear path of said flexible end section, said guide means being in retaining engagement with said flexible end section to guide said cutting means from said rectilinear path through said predetermined curved path as said rotary drill shaft means is advanced through said material.

18. A method for forming a curved bore within a material comprising the steps of:
(a) directing a bore forming means having a flexible distal end section with cutting means associated therewith through a rectilinear approach path at a given angle of approach to a surface to be bored;
(b) maintaining a portion of said bore forming means within said rectilinear path; and
(c) simultaneously guiding said flexible distal end section and said cutting means through a curved path, said cutting means forming a curved bore into said material, said bore forming device being capable of being advanced and retracted to form said curved bore without requiring an alteration of said angle of approach.

19. The method of claim 18, further comprising the steps of:
(a) simultaneously directing a second bore forming device having a flexible distal end section with cutting means associated therewith along a second rectilinear approach path which is generally parallel to said first rectilinear approach path; and guiding said the flexible distal end section in a common plane until said cutting means approach each other to form a curved bore.

20. An apparatus for drilling a curved bore through a material comprising:
   (a) a rotary drive means;
   (b) cutting means;
   (c) drill shaft mean shaving one end thereof adapted for connection to said rotary drive means, said drill shaft means having a distal flexible end section with said cutting means attached thereon;
   (d) mounting means for directing said drill shaft means along an approach path within said mounting means relative to a surface of said material; and
   (e) guide means carried by said mounting means to guide said flexible end section and said cutting means from said approach path along a curved path upon entry into said material, said drill shaft means being moved along said approach path with respect to said mounting means.

21. A method for forming a curved bore within a material, comprising the steps of:
   (a) directing a bore forming means having a flexible distal end section with cutting means associated therewith through an approach path relative to a surface to be bored:
   (b) maintaining a portion of said bore forming means along in said approach path; and
   (c) simultaneously guiding said flexible distal end section and said cutting means through a curved path, said cutting means forming a curved bore into said material, said bore forming device being capable of being advanced and retracted to form said curved bore without requiring an alteration of said orientation of said approach path.

22. An apparatus for drilling a curved bore within a material comprising:
   (a) rotary drive means;
   (b) cutting tip means;
   (c) drill shaft housing means;
   (d) drill shaft means adapted for connection at one end thereof to said rotary drive means, said drill shaft means having a distal flexible end section, said cutting tip means being attached to said flexible end section;
   (e) means mounting said flexible end section of said drill shaft means within said drill shaft housing means for reciprocal movement therein;
   (f) curved guide means located within said drill shaft housing means adjacent to said flexible end section;
   (g) means pivotally mounting said curved guide means within said drill shaft housing means for rotation along a curved path;
   (h) drive means for rotating said guide means; and
   (i) engaging means acting between said curved guide means and said flexible end section;
   (j) whereby rotation of said curved guide means advances said flexible end section and said cutting tip means along said curved path to form said curved bore.

23. The apparatus of claim 2, wherein:
   said means acting between said curved guide means and said flexible end section comprises engaging means to advance said flexible end section toward said material upon rotation of said curved guide means; whereby said flexible end section is pulled and guided through said curved path within said curved bore upon pivotal movement of said curved guide means.

24. The apparatus of claim 2, further comprising;
   (a) means mounted in said housing means for rotating said curved guide means along said curved path about said pivotal mounting means;
   (b) sliding connecting means located within said drill shaft means for permitting reciprocal movement of at least said flexible end section within said housing means during rotation thereof, said means acting between said curved guide means and said flexible end section comprising engaging means for advancing said flexible end section into said material as said curved guide means is rotated in one direction; and
   (c) spring biased return means within said slidable connecting means for returning said flexible end section and said cutting tip means to retracted position upon reverse rotation of said curved guide means.

25. The apparatus of claim 23, further comprising:
   (a) a hand held drive unit connected to said housing means, said hand held drive unit being adapted to mount rotary drive means thereto for rotation of said drill shaft means,
   (b) wherein said means for rotating said curved guide means comprises drive gear means mounted within said hand held unit drive unit, said drive gear means being activated by a trigger; said drive shaft means being drivingly connected to said drive gear means for rotating said curved guide means;
   (c) means to connect said drive shaft means to said drive means, said drive gear means being depressible in one direction to rotate said curved guide means within said curved bore; and
   (d) spring return means for returning said trigger to activate said gear means to drive said curved guide means in an opposite direction.

26. The apparatus of claim 25, wherein said curved guide means comprises:
   (a) a curved channel member having one side thereof open for reception of said flexible end section as said flexible end section advances;
   (b) said curved channel member having a predetermined curvature of said curved bore; and
   (c) said engaging means having a collar surrounding said flexible end section adjacent said cutting tip to retain said flexible end section within said curved channel member and to push said cutting tip means through said curved path to form said curved bore.

27. The apparatus of claim 24, further comprising:
   (a) first and second drill shaft means; and
   (b) first and second curved guide means, said first and said second curved guide means being generally arcuate, said means pivotally mounting said first and said second curved guide means within said housing for pivotal movement of said curved guide means within a substantially common plane to enable corresponding flexible end sections and said cutting tip means to travel along said curved path to form said curved bore.

28. The apparatus of claim 24, wherein said curved guide means is generally arcuate, and
   wherein said means for rotating said curved guide means is adapted to rotate said curved guide means to form said curved bore within said material.

29. The apparatus of claim 25, wherein said curved guide means is generally arcuate, and
   wherein said means for rotating said curved guide means is adapted to rotate said curved guide means to form said curved bore within said material.

30. The apparatus of claim 30, wherein said curved guide means comprises a radius arm connected at one end thereof to one end of said curved guide means and having another end thereof pivoted to one side of said housing means,
   slot means in one side of said housing means adjacent to said means for pivotally mounting said radius arm,
   said radius arm extending substantially a full width of said housing means and movable through approximately 180° between a first position extending through said slot means and outside said housing means and a second position normal to a longitudinal arm of said housing means within said housing means,
   whereby rotation of said radius arm from said first position to said second position rotates said curved guide means through approximately 180° to form said curved bore.

31. The apparatus of claim 30, further comprising:
   an anchor sleeve surrounding said housing means, said radius arm, and said curved guide means when in said first position; and
   means for temporarily pinning said anchor sleeve to said surface of said material in a desired location,
   whereby lateral displacement of said drill shaft housing means may be prevented during a drilling operation.

32. The apparatus of claim 30, further comprising:
   an anchor sleeve surrounding said housing means, and
   means for temporarily pinning said anchor sleeve to said surface of said material to be drilled in a desired location,
   said anchor sleeve having vertical slot means in register with a slot in said housing means, said slot in said anchor sleeve being at least twice a length of said radius arm,
   whereby said anchor sleeve may be affixed to said surface to be drilled, said housing means being inserted therein with said radius arm located between said first position and said second position, said arm rotating toward said first position through said slot and said housing means then being seated upon said surface of said material to be drilled.

33. The apparatus of claim 1, wherein said drill shaft means is mounted for reciprocating movement within said mounting means and relative thereto,
   said guide means being carried by said mounting means for movement relative thereto for guiding said flexible end section and said cutting means from said rectilinear path along said curved path.

34. The apparatus of claim 20, wherein said guide is carried by said mounting means for movement relative thereto for guiding said flexible end section and said cutting means from said approach path through said curved path.

35. A method for forming a curved bore with a drilling apparatus having a drill shaft means mounted therein with one end thereof adapted for connection to rotary drive means, said drill shaft means having a distal flexible end section with cutting means thereon, said method comprising the steps of:
   (a) directing said drill shaft means along an approach path within said drilling apparatus, said approach path and drilling apparatus having a specific orientation surface to be drilled, and
   (b) guiding said flexible end section and said cutting means from said approach path along a curved path,
   (c) whereby said drill shaft means may be advanced and retracted to form said curved bore without altering said orientation of said drilling apparatus and said approach path.

36. An apparatus for drilling a curved bore within a material, comprising:
   (a) rotary drive means;
   (b) cutting means;
   (c) drill shaft means having one end adapted for connection to said rotary drive means, said drill shaft means having a distal flexible end section with said cutting means attached thereto;
   (d) mounting means for directing said drill shaft means along in rectilinear path which is substantially normal to a surface of said material, and
   (e) guide means carried by said mounting means to guide said flexible end section and said cutting means from said rectilinear path along said curved path upon entry into the surface of the material to be drilled, said mounting means maintaining the remainder of the drill shaft in the rectilinear path throughout the drilling operation.

* * * * *